United States Patent
Syed

(10) Patent No.: US 10,086,026 B2
(45) Date of Patent: Oct. 2, 2018

(54) COMBINED HERBAL AND PHARMACEUTICAL COMPOSITION AND METHOD

(71) Applicant: Uwais M. Syed, River Edge, NJ (US)

(72) Inventor: Uwais M. Syed, River Edge, NJ (US)

( * ) Notice: Subject to any disclaimer, the term of this patent is extended or adjusted under 35 U.S.C. 154(b) by 84 days.

(21) Appl. No.: 15/193,945

(22) Filed: Jun. 27, 2016

(65) Prior Publication Data

US 2017/0368124 A1    Dec. 28, 2017

(51) Int. Cl.

| | | |
|---|---|---|
| A61K 36/00 | (2006.01) | |
| A61K 36/185 | (2006.01) | |
| A61K 31/045 | (2006.01) | |
| A61K 31/085 | (2006.01) | |
| A61K 31/135 | (2006.01) | |
| A61K 31/137 | (2006.01) | |
| A61K 31/167 | (2006.01) | |
| A61K 31/485 | (2006.01) | |
| A61K 36/28 | (2006.01) | |
| A61K 36/53 | (2006.01) | |
| A61K 36/725 | (2006.01) | |
| A61K 36/9068 | (2006.01) | |
| A61K 47/10 | (2017.01) | |
| A61K 47/12 | (2006.01) | |
| A61K 47/14 | (2017.01) | |
| A61K 47/34 | (2017.01) | |
| A61K 47/36 | (2006.01) | |
| A61K 47/18 | (2017.01) | |
| A61K 47/26 | (2006.01) | |

(52) U.S. Cl.
CPC .......... *A61K 36/185* (2013.01); *A61K 31/045* (2013.01); *A61K 31/085* (2013.01); *A61K 31/135* (2013.01); *A61K 31/137* (2013.01); *A61K 31/167* (2013.01); *A61K 31/485* (2013.01); *A61K 36/28* (2013.01); *A61K 36/53* (2013.01); *A61K 36/725* (2013.01); *A61K 36/9068* (2013.01); *A61K 47/10* (2013.01); *A61K 47/12* (2013.01); *A61K 47/14* (2013.01); *A61K 47/34* (2013.01); *A61K 47/36* (2013.01); *A61K 47/183* (2013.01); *A61K 47/26* (2013.01)

(58) Field of Classification Search
CPC ..................................................... A61K 36/00
See application file for complete search history.

(56) References Cited

U.S. PATENT DOCUMENTS

| | | |
|---|---|---|
| 5,248,503 A | 9/1993 | Emanuel-King |
| 5,834,000 A | 11/1998 | Yng-Wong |
| 6,592,896 B2 | 7/2003 | Rosenbloom |
| 8,367,146 B2 | 2/2013 | Lutz et al. |
| 8,986,756 B2 | 3/2015 | Lee |
| 9,205,122 B2 | 12/2015 | Cyr et al. |
| 2001/0011083 A1 | 8/2001 | Barr et al. |
| 2003/0124067 A1 | 7/2003 | Yue et al. |
| 2003/0147896 A1 | 8/2003 | Solanki |
| 2004/0086582 A1* | 5/2004 | Mitchell ............. A23F 3/163 424/756 |
| 2005/0192344 A1* | 9/2005 | Barberich ........... A61K 31/343 514/469 |
| 2005/0196473 A1 | 9/2005 | Cheng et al. |
| 2007/0110676 A1* | 5/2007 | Clymer .............. A61K 9/0043 424/45 |
| 2009/0068255 A1 | 3/2009 | Yu et al. |
| 2009/0263514 A1 | 10/2009 | Gopinathan |
| 2011/0318438 A1 | 12/2011 | Chung |
| 2013/0034542 A1* | 2/2013 | Ganter ............... A61K 38/40 424/130.1 |

FOREIGN PATENT DOCUMENTS

| | | | | |
|---|---|---|---|---|
| CN | 105194633 A | * | 12/2015 | |
| WO | WO 2010146601 A1 | * | 12/2010 | ............ A61K 9/006 |

OTHER PUBLICATIONS

Goodier Cosmetics LP:Sebrx Topical Analgesic; Internet, Drugs.com.,https://www.drugs.com/otc/112498/sebrx-topical-analgesic.html, Revised Dec. 2011; p. 1, ln 9-11; p. 2, ln 8,14;,Dallas,TX,USA.

* cited by examiner

*Primary Examiner* — Qiuwen Mi
(74) *Attorney, Agent, or Firm* — IDP Patent Services; Olav M. Underdal

(57) ABSTRACT

An herbal combination composition can include, herbal extracts, including combinations of: *Hyssopus officinalis, Zingiber officinale, Viola odorata, Ziziphus jujuba*, Chamomile, and *Ocimum tenuiflorum*; pharmaceutical compositions, including combinations of: dextromethorphan, guaifenesin, acetaminophen, phenylephrine, diphenhydramine; polyethylene glycol; propylene glycol; poloxamer 407; ethylenediaminetetraacetic acid; methyl paraben; potassium sorbate; propyl paraben; xanthan gum; citric acid; anhydrous citric; and purified acetate buffered water. Also disclosed is a method for manufacture of an herbal combination composition, including dissolving herbal extracts, adding poloxamer, adding pharmaceutical compositions, adding acetate buffer, adding xanthan gum gel, adding acetate buffer.

16 Claims, 1 Drawing Sheet

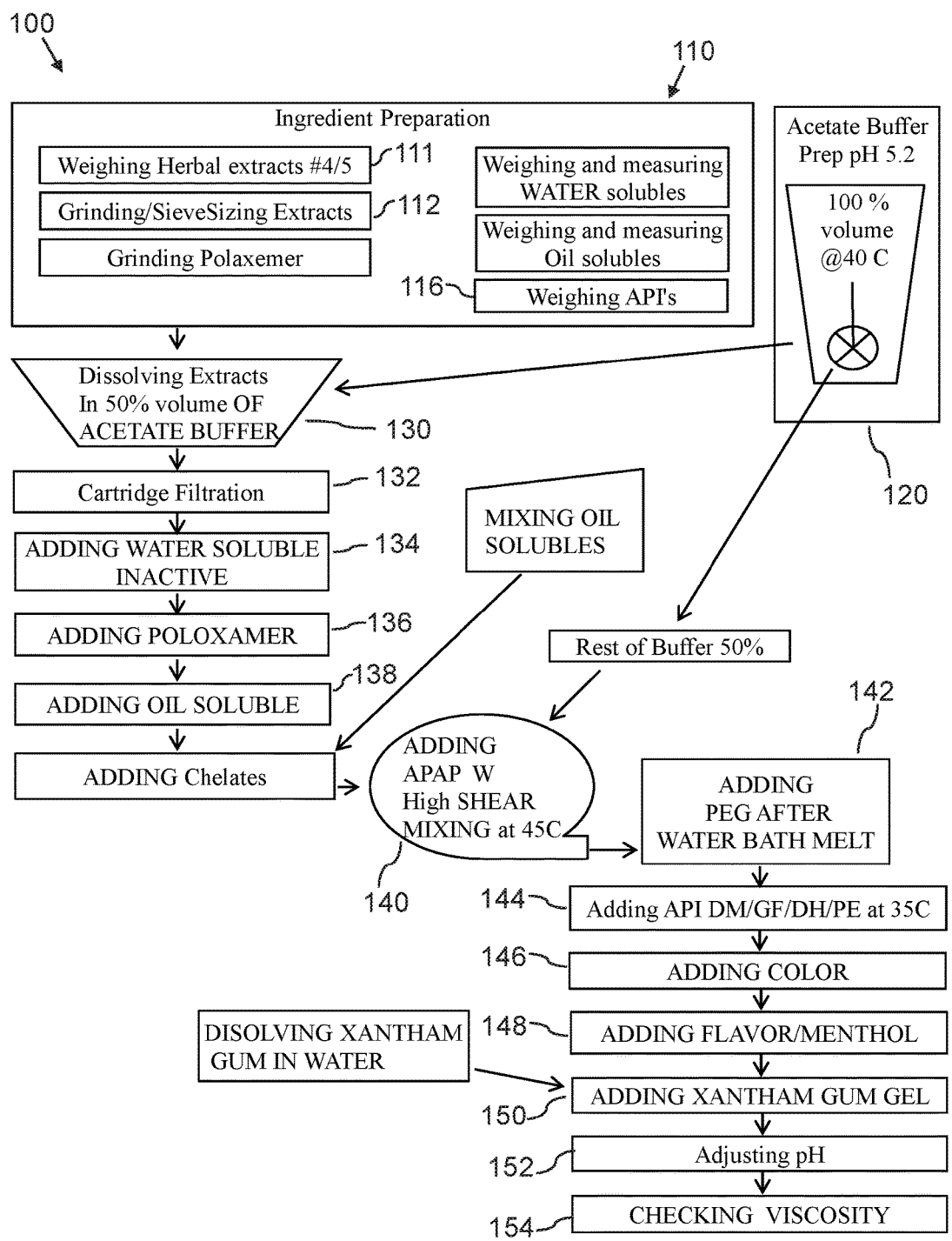
Process for manufacture of an herbal combination composition

COMBINED HERBAL AND PHARMACEUTICAL COMPOSITION AND METHOD

CROSS-REFERENCE TO RELATED APPLICATIONS

N/A

FIELD OF THE INVENTION

The present invention relates generally to the field of herbal medicines and remedies, and more particularly to methods and formulation for combining herbal extracts with conventional pharmaceutical compositions.

BACKGROUND OF THE INVENTION

The continuously growing herbal use in international market shows the beneficial use of herbal medicines as a complement to general pharmaceuticals. This situation has left consumers to wander around shelves to self-select different herbal and pharmaceutical supplements and medications separately, as they are in many cases not available on the same shelf of the same store. Patients struggle to get a good synergistic combination of herbal and pharmaceuticals; as in most cases there are no combinations available in ready-made combined forms. Most of the time consumers/patients remain unsuccessful in diminishing their ailment related sufferings and pain, which could be possible by using the benefits of both herbal medicines and conventional pharmaceuticals in a single formulation.

Combining herbals with pharmaceuticals is not a trivial undertaking in terms of product quality, consistency, and shelf life. Herbal extracts are not comprised of single molecule but are rather composed of a variety of molecules of different pharmaceutical classes. Herbal extracts constitute combinations of enzymes, co-enzymes, catalysts, volatile, fixed oils, flavonoids, amino acids, complexing agents, saponins, triterpinoids, tannins, sesquiterpenes, monoterpenes, etc. These chemical moieties are in many cases reactive to the active pharmaceuticals and cause their degradation in a small period of time, resulting in separation of layers, suspension, turbidity, discoloration, and in some cases change of the active pharmaceuticals into a toxic material.

This complex situation needs a pre-study of the compatible herbals selection, optimization of the quantity added of each herbal extract besides the addition of formulation excipients such as solubilizes, flavors, humectants, sweetening agents, and preservatives to the active pharmaceuticals; so that a stable formulation can be achieved.

Combining herbals with pharmaceuticals is not always successful but need to be proven by the results of a detailed chemical and microbiological stability studies. United States pharmacopeia provides acceptance criteria in terms of potency of the active pharmaceuticals, and the absence of microbiological growth during the label claimed shelf life. The average shelf life for a liquid formulation is eighteen months. During the shelf life product must maintain its physicochemical attributes within USP acceptance criteria. Shelf stability is not only important but a robust manufacturing technique with detailed steps is required to avoid complexation, suspension, loss of flavoring agents, volatiles, mixing of oils with water, avoiding complexation leading to precipitation, separation of layers, etc.

As such, considering the foregoing, it may be appreciated that there continues to be a need for novel and improved devices and methods for combining herbal extracts with pharmaceutical compositions.

SUMMARY OF THE INVENTION

The foregoing needs are met, to a great extent, by the present invention, wherein in aspects of this invention, enhancements are provided to the existing model of combining herbal extracts with pharmaceutical compositions.

Aspects of this invention provide combined/fused formulations of single therapies of medicinal herbal extracts and synergistic cold and cough pharmaceuticals.

Another aspect of this invention also defines a detailed stepwise method of manufacturing ensuring reproducibility of the end products with the same physicochemical attributes. The invented product maintains microbiological as well as chemical quality, meeting all standards of the current United States Pharmacopeia (USP) during its label claimed shelf life.

In yet another aspect, this invention is also coupled with the invention of a new single robust analytical method to analyze potency of all of the individual active ingredients in the presence of herbal actives. The method is capable of identifying and quantifying active pharmaceuticals within complex composition of the formulation in significantly low retention time and high resolution as compared to many other methods/combination of methods reported in literature for different active ingredients.

In related aspects, this invention is furnishing new knowledge in terms of manufacturing technique, selection of herbs, compatibility of herbs with active pharmaceutical ingredients of formulation by utilizing newly invented robust analytical methods as elements of the entire innovation.

In other related aspects, the usefulness of invention hinges on bringing the benefits of the fused/combined medicinal herbal and pharmaceuticals formulations therapy to the population suffering from common cold, influenza, seasonal allergies, etc.

In an aspect, an herbal combination composition, can include:
a) herbal extracts, including at least one or a combination of: *Hyssopus officinalis; Zingiber officinale; Viola odorata; Ziziphus jujuba*; Chamomile; *Ocimum tenuiflorum*; and
b) pharmaceutical compositions, including at least one or a combination of: Dextromethorphan; Guaifenesin; Acetaminophen; Phenylephrine hydrochloride; Diphenhydramine hydrochloride.

In an aspect, a method for manufacture of an herbal combination composition can include:
a) dissolving herbal extracts;
b) adding poloxamer;
c) adding pharmaceutical compositions;
d) adding acetate buffer;
e) adding xanthan gum gel; and
f) adding acetate buffer.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 1 is a flowchart illustrating steps that may be followed, in accordance with one embodiment of a method or process of manufacture of an herbal combination composition.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of various embodiments of an herbal combination composition and methods for its manufacture.

In various embodiments, the herbal combination composition can be a mixture, including a powder, which can be a granule powder; a syrup, emulsion, or suspension with an established viscosity, color, pH and flavors. Oily parts must be dispersed into fine globules within syrup with the help of an emulsifying agent. Therefore, an acceptable formulation cannot be achieved simply by a juice mixer technique. It needs step wise control and testing during manufacturing till a stable formulation is achieved for a shelf life stability testing at various temperatures and relative humidity to mimic shelf life conditions of different countries. Higher temperature and relative humidity study is an alternative to have an accelerated study for a short period of time to apply a linear regression for the extrapolated time period. Once studies are successfully completed, then the data is considered as the new knowledge to satisfy the claim labels of the active pharmaceuticals in the mixed formulation.

In related embodiments, microbial and fungal contamination control of the herbs are other major challenges as the source of the herbs are natural agricultural fields rather than a controlled manufacturing of a chemical plant. A specific preservative or a combination of preservatives in the correct quantities needs to be selected and employed based on the incoming quality of raw herbal extracts from the extract manufacturers; to avoid any fungal or microbial growth in the combined formulation.

In further related embodiments, in order to make stable formulations the particulate size of the herb extracts needs to be maintained and particles larger than 0.5 micron needs to be eliminated by filtration to avoid suspension, and segregation.

In other further related embodiments, solubilizing different moieties of the extracts is not as simple as one or few molecules of the active pharmaceuticals. It needs the use of co-solvents, solubilizes, chelating agents, emulsifying agents and experimenting those until an optimized combination is satisfied. A new knowledge establishes here as the part of the invention.

In further related embodiments, an herbal combination composition can include chelating agents, co-solvents, preservatives, solubilizes, and other excipients. Polyethylene glycol 1000, or PEG 600-1000, can be included to thicken a syrup with Xanthan gum to establish a target viscosity of the syrup.

In a further related embodiment, an acetate buffer and/or citric acid can be used to maintain pH of the herbal combination composition around 5.0.

In further related embodiments, a high shear mixing technique can be used to produce a homogenized solution, such as shown in the process flow diagram depicted in FIG. 1. Heating/Cooling and RPM of the agitators can be varied to adjust the process and hot water jacketed heating and cooling can be configured at different levels of the manufacturing as defined in the process flow diagram shown in FIG. 1.

In a related embodiment, the herbal combination composition can be formulated for diabetic patients, such that the herbal combination composition includes artificial non sugar based sweetener, such as saccharine sodium, sucralose, etc.

In various embodiments, the herbal combination composition can include Hyssop, Ginger, *Viola odorta*, jujube, chamomile, Holy Basil (*Ocmium tenuiflorum*), having the following characteristics:

a) *Hyssopus officinalis* (Hyssop) has been indicated in the Natural Medicines for cough, common cold, respiratory infections, and sore throat. It is considered GRAS (generally recognized as safe) by the US Food and Drug Administration;

b) *Zingiber officinale* (Ginger) is reported as GRAS by the FDA. It has been indicated in the natural medicines for upper respiratory tract infections, cough, bronchitis, nausea, and headache. The active part of ginger is ginger root. It includes gingerol, gingerdione, shogaol, sesquiterpine, and monoterpene volatile oils.

c) *Viola odorata* (Sweet violet) is indicated in the natural medicines for chronic and acute bronchitis, bronchial asthma, acute and chronic mucous inflammation, cold symptom hoarseness, chest spastic and whooping cough;

d) *Ziziphus jujuba* (Jujube or red date) is indicated for cold and cough; especially the calming nature has reported providing stress relief, and promoting sleep;

e) Chamomile, which can include extracts of various species of *Asteraceae*, is reported as GRAS by the FDA. Chamomile extract has been indicated for respiratory tract irritation, allergic rhinitis, and nasal membrane inflammation;

f) Holy Basil (*Ocimum tenuiflorum*) has been indicated for its short term (4 to 6 weeks) use as a safe remedy for common cold, influenza, swine flu, asthma, bronchitis, and fever because of its anti-infective properties.

In related embodiments, a detailed scientific review of the herbal constituents has provided support for selecting and optimize these herbs in the range of 1-2% individually of the clinical dose, not exceeding more than 7% of the total herbal content. Formulation was put on a long term stability study at 25±2 degree Celsius and relative humidity of 60±5% as required by United States Pharmacopeia. The label claimed potency was found within 110% and 90% of the label claim at 21 months long term samples.

Development and research of related embodiments, led to development of a robust analytical spectroscopic High Pressure Liquid Chromatography method to test each sample for all active pharmaceuticals in the presence of all herbal constituents and excipients with highest clear resolution of each individual active ingredient. The overlapping peaks of many unknown peaks from the herbal mixture makes it extremely difficult to separate and analyze each individual pharmaceutical active with required resolution and minimum shift with respect to the known concentration of the reference material.

In an embodiment, an herbal combination composition can include:
a) at least one herbal extract, which can include at least one extract of:
  i. *Hyssopus officinalis;*
  ii. *Zingiber officinale;*
  iii. *Viola odorata;*
  iv. *Ziziphus jujuba;*
  v. Chamomile;
  vi. *Ocimum tenuiflorum;* or
  vii. A combination of these.
b) At least one pharmaceutical composition, which can include:
  i. Dextromethorphan;
  ii. Guaifenesin;
  iii. Acetaminophen;
  iv. Phenylephrine, such as Phenylephrine hydrochloride;
  v. Diphenhydramine, such as Diphenhydramine hydrochloride; and optionally at least one or a combination of
c) At least one chelating agent, such as Polyethylene glycol;
d) Poloxamer;
e) Xanthan gum;
f) An antioxidant, which can include Propyl gallate;
g) An Acetate buffer solution;
h) Coloring ingredients;
i) Flavoring ingredients; and
j) Sweeteners.

In related embodiments, the herbal extracts can include powder extracts, solvent extracts, and/or essential oil extracts.

In related embodiments, the herbal combination composition can be provided in a packet size as a liquid, mixture, or powder; in liquid, capsule or tablet dosage forms; wherein a tablet, capsule, a predetermined weight of a mixture or powder, or a predetermined liquid volume are defined as a single dosage.

In related embodiments, a liquid single-dosage formulation of the herbal combination composition can be 5 ml (1 teaspoon), 10 ml (2 teaspoons), 15 ml (3 teaspoon), or 20 ml (4 teaspoon) of the final formulation package size, 120, 240 ml, or another dosage volume.

In related embodiments, the herbal extracts of the herbal combination composition can be pure extracts with a 4:1 to 6:1 extraction ratio range.

In related embodiments, the optional coloring ingredients of the herbal combination composition can include at least one or a combination of: FD&C Green #3, FD&C Yellow #6, FD&C Blue #1, and FDC&C RED #40.

In related embodiments, the optional flavoring ingredients of the herbal combination composition can include at least one or a combination of: grape flavor, honey flavor, berry flavor, cherry Flavor, lemon flavor, mango flavor, and strawberry flavor. In further related embodiments, the flavoring ingredients can comprise no more than 2% by volume of a single-dosage volume of the herbal combination composition.

In a related embodiment, an herbal combination composition, as specified in percentage of total volume of 240 ml of the herbal combination composition and in specific volume, can include:
1) *Viola odorata* extract in 1% by volume or 2.4 ml;
2) Hyssop extract in 1% by volume or 2.4 ml;
3) *Ocimum tenuiflorum* (Tulasi) extract liquid 1:10 in 0.5% by volume or 1.2 ml;
4) Jujube extract in 0.5% by volume or 1.2 ml;
5) Ginger extract in 1.04% by volume or 2.5 ml;
6) Menthol in 0.05% by volume or 0.12 ml;
7) Chamomile in 0.521% by volume or 1.25 ml;
8) Polyethylene glycol 600 to 1000 in 5% by volume or 12 ml;
9) Sucralose in 0.4% by volume or 0.96 ml;
10) Dextromethorphan in range of 5-20 milligram;
11) Glycerine in 5% by volume or 12 ml;
12) Propylene glycol in 3% by volume or 7.2 ml;
13) Polaxamer, which can be Polaxamer 407 in 0.208% by volume or 0.5 ml;
14) Ethylenediaminetetraacetic acid (EDTA) in 0.2% by volume or 0.48;
15) Methylparaben in 0.018% by volume or 0.043 ml;
16) Potassium sorbate in 0.1% by volume or 0.24 ml;
17) Propylparaben in 0.02% by volume or 0.048 ml;
18) Cherry flavor/Any other suitable flavor agent in 1% by volume or 2.4 ml
19) Sorbitol in 2.5% by volume or 6 ml;
20) Xanthan gum in 0.075% by volume or 0.18 ml;
21) Saccharin in 0.02% by volume or 0.048 ml;
22) Citric acid in 5% by volume or 12 ml;
23) Guaifenesin in a range of 50-400 milligram;
24) Acetaminophen in a range of 160-650 milligram;
25) Phenylephrine HCl in a range of 2.5-10 milligram;
26) Sorbitol in 5% by volume or 12 ml;
27) Diphenhydramine HCl in a range of 6.25-50 milligram;
28) FD&C Green in 0.00125% by volume or 0.003 ml;
29) Purified acetate buffered water; in volume to reach total volume of 240 ml; and/or
30) Anhydrous citric Acid 0.05-0.1% to adjust pH to target value.

In a further related embodiment, the herbal combination composition can further include sucrose, as a substitute for or in addition to Saccharin and/or Sorbitol.

In a further related embodiment, the herbal combination composition can further include sucralose, as a substitute for or in addition to Saccharin and/or Sorbitol.

In a related embodiment, the herbal combination composition in a single-dosage formulation can include at least one or a combination of:
1) *Viola odorata* extract in a range of 0.25%-1.5% by volume;
2) Hyssop extract in a range of 0.25%-1.5% by volume;
3) Tulasi extract liquid 1:10 in a range of 0.25%-0.75% by volume;
4) Jujube extract in a range of 0.25%-1% by volume;
5) Ginger extract in a range of 0.25%-1.56% by volume;
6) Menthol extract in a range of 0.025%-0.075% by volume;
7) Chamomile extract in a range of 0.25%-1% by volume;
8) Polyethylene glycol 1000 in a range of 2.5%-7.5% by volume;
9) Sucralose in a range of 0.2%-0.6% by volume;
10) Dextromethorphan in a range of 5-20 mg;
11) Glycerine in a range of 2.5%-7.5% by volume;
12) Propylene glycol in a range of 1.5%-4.5% by volume;
13) Polaxamer, which can be Polaxamer 407 in a range of 0.1%-0.325% by volume;
14) eDTA in a range of 0.1%-0.3% by volume;
15) Methylparaben in a range of 0.009%-0.03% by volume;
16) Potassium sorbate in a range of 0.05%-0.15% by volume;
17) Propylparaben in a range of 0.01%-0.03% by volume;
18) Cherry flavor/Any other suitable flavor agent in a range of 0.5%-1.5% by volume;
19) Sorbitol in a range of 1.2%-3.8% by volume;
20) Xanthan gum in a range of 0.038%-0.113% by volume;
21) Saccharin in a range of 0.01%-0.03% by volume;
22) Citric acid in a range of 2.5%-7.5% by volume;
23) Guaifenesin in a range of 50-400 mg;
24) Acetaminophen in a range of 160-650 mg;
25) Phenylephrine HCl in a range of 2.5-10 mg;
26) Sorbitol in a range of 2.5%-7.5% by volume;
27) Diphenhydramine HCl in a range of 6.25-50 mg;
28) Propyl Gallate in a range of 0.05%-0.2% by volume;
29) FD&C Green Grape flavor in a range of 0.001%-0.002% by volume;
30) Anhydrous citric Acid in a range of 0.038%-0.113% by volume; and/or
31) Purified acetate buffered water in a range of 32%-96% by volume;
wherein ingredient ranges, if not specified by weight or volume, are listed in percentage by volume of the herbal combination composition for a single-dosage formulation of the herbal combination composition.

In some embodiments, herbal combination composition can include propylene glycol in a range of 1.5%-14% in percentage of total volume of the herbal combination composition. In further related embodiments, a higher content of propylene glycol, up to 14% by volume and in some cases higher, can serve to increase the stability when acetaminophen (APAP) is included as an ingredient.

In related embodiments, the herbal combination composition in a single-dosage formulation can include at least one or a combination of:
1) *Viola odorata* extract in a range of 0.25%-1.5% by weight;
2) Hyssop extract in a range of 0.25%-1.5% by weight;
3) Tulasi extract liquid 1:10 in a range of 0.25%-0.75% by weight;
4) Jujube extract in a range of 0.25%-1% by weight;
5) Ginger extract in a range of 0.25%-1.5% by weight;
6) Menthol extract in a range of 0.022%-0.075% by weight;
7) Chamomile extract in a range of 0.25%-1% by weight;
8) Polyethylene glycol 600-1000 in a range of 2.5%-8% by weight;
9) Sucralose in a range of 0.2%-1% by weight;
10) Dextromethorphan in a range of 5-20 mg;
11) Glycerine in a range of 2.5%-9% by weight;
12) Propylene glycol in a range of 1.5%-4.5% by weight;
13) Polaxamer, which can be Poloxamer 407 in a range of 0.1%-0.3% by weight;
14) eDTA in a range of 0.1%-0.3% by weight;
15) Methylparaben in a range of 0.01%-0.04% by weight;
16) Potassium sorbate in a range of 0.05%-0.2% by weight;
17) Propylparaben in a range of 0.01%-0.03% by weight;
18) Cherry flavor/Any other suitable flavor agent in a range of 0.5%-1.5% by weight;
19) Sorbitol in a range of 1.2%-5.5% by weight;
20) Xanthan gum in a range of 0.04%-0.165% by weight;
21) Saccharin in a range of 0.01%-0.03% by weight;
22) Citric acid in a range of 2.5%-12% by weight;
23) Guaifenesin in a range of 50-400 mg;
24) Acetaminophen in a range of 160-650 mg;
25) Phenylephrine HCl in a range of 2.5-10 mg;
26) Sorbitol in a range of 2.5%-11% by weight;
27) Diphenhydramine HCl in a range of 6.25-50 mg;
28) FD&C Green Grape flavor in a range of 0.001%-0.002% by weight;
29) Propyl Gallate in a range of 0.05%-0.2% by weight;
30) Anhydrous citric Acid in a range of 0.038%-0.18% by weight; and/or
31) Purified acetate buffered water in a range of 30%-96% by weight;
wherein ingredient ranges, if not specified by weight, are listed in percentage by weight of the herbal combination composition for a single-dosage formulation of the herbal combination composition.

In related embodiments, the herbal combination composition in a single-dosage formulation can include at least one or a combination of:
1) *Viola adorta* extract in a range of 1.2-3.6 gram;
2) Hyssop extract in a range of 1.2-3.6 gram;
3) Tulasi extract liquid 1:10 in a range of 0.6-1.8 gram;
4) Jujube extract in a range of 0.6-1.8 gram;
5) Ginger extract in a range of 1.25-3.75 gram;
6) Menthol in a range of 0.0534-0.1602 gram;
7) Chamomile extract in a range of 0.625-1.875 gram;
8) Polyethylene glycol 600-1000 in a range of 6.6-19.8 gram;
9) Sucralose in a range of 0.8112-2.4336 gram;
10) Dextromethorphan in a range of 0.005-0.02 gram;
11) Glycerine in a range of 7.554-22.662 gram;
12) Propylene glycol in a range of 3.47508-10.42524 gram;
13) Polaxamer, which can be Polaxamer 407, in a range of 0.25-0.75 gram;
14) eDTA in a range of 0.2064-0.6192 gram;
15) Methyl paraben in a range of 0.02967-0.08901 gram;
16) Pottasium sorbate in a range of 0.1632-0.4896 gram;
17) Propyl paraben in a range of 0.02544-0.07632 gram;
18) Cherry flavor/Any other suitable flavor agent in a range of 1.2-3.6 gram;
19) Sorbitol in a range of 4.47-13.41 gram;
20) Xanthan gum in a range of 0.135-0.405 gram;
21) Saccharin in a range of 0.019872-0.059616 gram;
22) Citric acid in a range of 9.96-29.88 gram;

23) Guafanesin in a range of 0.05-0.4 gram;
24) Acetaminophen in a range of 0.16-0.65 gram;
25) Phenylephrine HCl in a range of 0.0025-0.01 gram;
26) Sorbitol in a range of 8.94-26.82 gram;
27) Diphenhydramine in a range of 0.00625-0.05 gram;
28) FD&C Green Grape flavor in a range of 0.0015-0.0045 gram;
29) Propyl Gallate in a range of 0.145-0.45 gram;
30) Anhydrous citric Acid in a range of 0.1494-0.4482 gram;
31) Purified acetate buffered water in a range of 76.686-230.058 gram.

In an embodiment, a method for manufacture of an herbal combination composition 100, as shown in FIG. 1, can include, all or a combination of:
a) Ingredient preparation 110, including:
  1) Weighing of herb extracts 111;
  2) Sieving of herbs to mesh 112;
  3) Weighing of active pharmaceutical ingredients 116;
b) Preparing acetate buffer 120, which includes preparation of enough acetate buffer to mix and dissolve extracts and active pharmaceuticals, use for make-up volume, and use for dilution of the solution under manufacture;
c) Dissolving herbal extracts 130, wherein the extracts are dissolved and mixed with 50% volume of the acetate buffer at 35° C., with gentle stirring for a predetermined period, which can be one hour, or between 15 minutes and 3 hours;
d) Filtering solution 132, wherein the solution is filtered, for example with a cartridge filter, which can be a 0.5 micron cartridge filter;
e) Adding water soluble inactive ingredients 134;
f) Adding poloxamer 136, wherein crushed poloxamer is added to the solution during continuing stirring, wherein the crushed poloxamer is made by grinding poloxamer beads into small particles, wherein the poloxamer is selected from the group of nonionic triblock copolymers composed of a central hydrophobic chain of polyoxypropylene (poly(propylene oxide)) flanked by two hydrophilic chains of polyoxyethylene (poly(ethylene oxide)), or a composition of these;
g) Add sorbitol, potassium sorbate, and sucralose to stirring extract solution;
h) Add oil soluble propyl paraben 138, which is dissolved in mixture of propylene glycol and glycerin;
i) Add Saccharin and ethylenediaminetetraacetic acid (EDTA);
j) Adding acetaminophen 140, by raising temperature to 45° C., or 40° C.-50° C., and continuing brisk agitation, while adding acetaminophen in 3 parts until all parts are dissolved. Use high shear mixer to homogenize solution;
k) Adding Polyethylene Glycol 142 during high shear mixing, such that the Polyethylene Glycol, for example as PEG 600-1000, is pre-melted, for example in water jacketed vessel;
l) Adding Dextromethorphan, Guaifenesin, diphenhydramine HCl, Phenylephrine HCl 144, as per a predetermined single-dosage formulation and stir and dissolve for 45 minutes, or 15-75 minutes, at 40° C., or 35° C.-45° C., and then adding another 30% of the acetate buffer;
m) Adding coloring and flavoring agents 146 148. If foaming occurs, add Tween 80;
n) Dissolving and adding menthol. This can be done during or after adding coloring and flavoring 146 148;
o) Adding xanthan gum gel 150 with brisk stirring, wherein the xanthan gum gel is made by dissolving xanthan gum in water;
p) Adding acetate buffer to produce the final target volume;
q) Check the Ph;
r) Adjusting pH 152 to a target Ph value by using USP anhydrous citric acid, such that the target Ph can be in a range of 4.9-5.3, 5.0-5.2, or about 5.1 Ph; and
s) Checking final viscosity 154.

In a related embodiment, an UV/HPLC spectroscopic gradient method can include:
a) In a mobile phase C: mixing 80% of water with 20% methanol, triethylamine 0.1%, and adjust pH with phosphoric acid to 3.
b) In a mobile phase D (for final volume of 500 ml): dissolving 0.55 grams of 1 octane sulfonic acid in 50 ml of water, then filtering it, adding 250 ml of HPLC grade water, add 0.1% TEA (trimethylamine), then adding MeCN (acetonitrile) to reach a final volume of 500 ml. Finally, adjusting pH to 3 using phosphoric acid;
wherein references of active components are made in 10% methanol. Test solutions are diluted to the same reference strengths compared to active references for a direct peak height or area ratio calculation, thus allowing determination whether the test solution's active ingredient is within 90% to 110% of the active reference. A gradient method starting at 1.5 ml/minute flow rate of the combination of C:D (20:80) at the detection wavelength of 264 and changing to flow rate to 1.0 and the detection wavelength to 214 at 4 minutes time is followed and executed with an automated data and equipment control/acquisition system. The method elucidates all peaks within 15 minutes and is ready for next injection after a needle purge.

A Phenomenox™ brand column Luna® 5 μm C18(2) 100 Å, LC Column 250×4.6 mm can for example be used and maintained at 28° C.

In related testing of embodiments of the herbal combination composition, Phenylephrine HCl test samples and reference concentrations peak areas were found to be within a normal acceptance criteria range.

In related testing of embodiments of the herbal combination composition, Guaifenesin test samples and reference concentrations peak areas were found to be within a normal acceptance criteria range.

In related testing of embodiments of the herbal combination composition, Acetaminophen test samples and reference concentrations peak areas were found to be within a normal acceptance criteria range.

In related testing of embodiments of the herbal combination composition, Dextromethorphan test samples and reference concentrations peak areas were found to be within a normal acceptance criteria range.

In related testing of embodiments of the herbal combination composition, Diphenhydramine test samples and reference concentrations peak areas were found to be within a normal acceptance criteria range.

In related testing of embodiments of the herbal combination composition, no microbial growth was shown in formulations with and without Diphenhydramine. Microbial growth was observed in the +Ve control plate at the end of USP defined incubation period and temperature.

Here has thus been described a multitude of embodiments of the herbal combination composition, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. An herbal combination composition, comprising:
   a) herbal extracts comprising the combination of:
      Hyssopus officinalis;
      Zingiber officinale;
      Viola odorata;
      Ziziphus jujuba;
      chamomile; and
      Ocimum tenuiflorum; and
   b) at least one pharmaceutical composition, comprising:
      dextromethorphan in the range of 5-20 milligram;
      acetaminophen in the range of 160-650 milligram; and
      phenylephrine hydrochloride in the range of 2.5-10 milligram.

2. The herbal combination composition of claim 1, wherein the at least one herbal extract comprises:
   a) the Viola odorata in a percentage by volume of the herbal combination composition range of 0.5%-1.5%;
   b) the Hyssopus officinalis in a percentage by volume of the herbal combination composition range of 0.5%-1.5%;
   c) the Ocimum tenuiflorum in a percentage by volume of the herbal combination composition range of 0.25%-1%;
   d) the Ziziphus jujuba in a percentage by volume of the herbal combination composition range of 0.25%-1%;
   e) the Zingiber officinale in a percentage by volume of the herbal combination composition range of 0.5%-1.56%; and
   f) the chamomile in a percentage by volume of the herbal combination composition range of 0.25%-1%.

3. The herbal combination composition of claim 1, further comprising:
   polyethylene glycol in a percentage by volume of the herbal combination composition range of 2.5%-7.5%;
   wherein the polyethylene glycol has a molecular weight of 500-1500 g/mol.

4. The herbal combination composition of claim 1, further comprising:
   propylene glycol in a percentage by volume of the herbal combination composition range of 1.5%-14.5%.

5. The herbal combination composition of claim 1, further comprising:
   polaxamer 407 in a percentage by volume of the herbal combination composition range of 0.1%-0.3%.

6. The herbal combination composition of claim 1, further comprising:
   ethylenediaminetetraacetic acid in a percentage by volume of the herbal combination composition range of 0.1%-0.3%.

7. The herbal combination composition of claim 1, further comprising:
   methyl paraben in a percentage by volume of the herbal combination composition range of 0.009%-0.027%.

8. The herbal combination composition of claim 1, further comprising:
   potassium sorbate in a percentage by volume of the herbal combination composition range of 0.05%-0.15%.

9. The herbal combination composition of claim 1, further comprising:
   propyl paraben in a percentage by volume of the herbal combination composition range of 0.01%-0.03%.

10. The herbal combination composition of claim 1, further comprising:
    xanthan gum in a percentage by volume of the herbal combination composition range of 0.038%-0.113%.

11. The herbal combination composition of claim 1, further comprising:
    citric acid in a percentage by volume of the herbal combination composition range of 2.5%-7.5%.

12. The herbal combination composition of claim 1, further comprising:
    propyl gallate in a percentage by volume of the herbal combination composition range of 0.05%-0.2%.

13. The herbal combination composition of claim 1, further comprising:
    anhydrous citric acid in a percentage by volume of the herbal combination composition range of 0.038%-0.113%.

14. The herbal combination composition of claim 1, further comprising:
    purified acetate buffered water in a percentage by volume of the herbal combination composition range of 32%-96%.

15. The herbal combination composition of claim 1, wherein the at least one pharmaceutical composition comprises:
    a) the dextromethorphan in range of 5-20 milligram;
    b) guaifenesin in a range of 50-400 milligram;
    c) the acetaminophen in a range of 160-650 milligram;
    d) phenylephrine hydrochloride in a range of 2.5-10 milligram; and
    e) diphenhydramine hydrochloride in a range of 6.25-50 milligram.

16. An herbal combination composition, comprising:
    a) herbal extracts comprising the combination of:
       Viola odorata in a percentage by volume of the herbal combination composition range of 0.5%-1.5%;
       Hyssopus officinalis in a percentage by volume of the herbal combination composition range of 0.5%-1.5%;
       Ocimum tenuiflorum in a percentage by volume of the herbal combination composition range of 0.25%-1%;
       Ziziphus jujuba in a percentage by volume of the herbal combination composition range of 0.25%-1%;
       Zingiber officinals in a percentage by volume of the herbal combination composition range of 0.5%-1.56%; and
       chamomile in a percentage by volume of the herbal combination composition range of 0.25%-1%; and
    b) at least one pharmaceutical composition, comprising:
       dextromethorphan;
       acetaminophen; and
       phenylephrine.

* * * * *